United States Patent [19]

Kasahara et al.

[11] 4,295,853

[45] Oct. 20, 1981

[54] METHOD FOR MEASURING PEROXIDIC SUBSTANCES

[75] Inventors: Shizuka Kasahara, Amagasaki; Kazuhiko Yamanishi, Tokyo; Toshiro Hanada; Kuniaki Tokuda, both of Kawagoe; Shinzo Kobatake, Ibaraki, all of Japan

[73] Assignee: Wako Pure Chemical Industries, Ltd., Osaka, Japan

[21] Appl. No.: 974,148

[22] Filed: Dec. 29, 1978

[30] Foreign Application Priority Data

Dec. 29, 1977 [JP] Japan ............................... 52-159070
Feb. 28, 1978 [JP] Japan ............................... 53-22313

[51] Int. Cl.[3] ..................... G01N 31/22; G01N 33/52; G01N 33/92

[52] U.S. Cl. .................................... 23/230 B; 23/909; 435/11; 435/4

[58] Field of Search ..................... 23/230 B, 901, 909, 23/925, 932; 435/10, 11, 14, 28, 4

[56] References Cited

U.S. PATENT DOCUMENTS

| | | | |
|---|---|---|---|
| 3,630,680 | 12/1971 | Rittesdorf et al. | 23/230 B |
| 3,979,262 | 9/1976 | Hamziker | 435/28 X |
| 4,066,403 | 1/1978 | Bruschi | 23/230 B |
| 4,098,574 | 7/1978 | Dappen | 23/230 B X |
| 4,119,405 | 10/1978 | Lam | 23/230 B |

FOREIGN PATENT DOCUMENTS

| | | | |
|---|---|---|---|
| 2509156 | 9/1975 | Fed. Rep. of Germany | 23/230 B |

OTHER PUBLICATIONS

Colorimetric Det. of Org. Peroxides; Eiss et al.; Anal. Chem., vol. 31, No. 9, 9 1959, pp. 1558–1560.

Det. of Fat Peroxides in the Presence of Phospholipids; L. Hartman, Analy. Abstract #775, vol. 2, #3, 1955.

*Primary Examiner*—Michael S. Marcus
*Attorney, Agent, or Firm*—Armstrong, Nikaido, Marmelstein & Kubovcik

[57] ABSTRACT

Peroxidic substances in a sample, e.g. one or more peroxidic substances in fats and oils or in an organic material, lipoperoxides in a living sample, etc. can be determined, directly in a sample or after extracting the lipoperoxides from a living sample with a solvent, by contacting the peroxidic substances with an oxidizable color reagent in the presence of a metallic compound produced from a metal which is able to have two or more valences to produce color, and measuring degree of coloring colorimetrically.

8 Claims, No Drawings

METHOD FOR MEASURING PEROXIDIC SUBSTANCES

This invention relates to a method for measuring the amount of peroxidic substances in a sample, e.g. in a living sample, in fats and oils, in an organic material, etc.

Peroxidic substances, particularly lipoperoxides have been regarded as taking harmful action on living organisms. Recently relationship between the production of the lipoperoxides in a living organism and senility has been discussed and participation of the lipoperoxides in the progress of clinical symptom of arteriosclerotic disease, diabetes, mellitus, etc. has been studied. These studies have led to a thought that the lipoperoxides become a cause of regressive change in combination with senility and accelerate arteriosclerosis.

Since there are a large number of higher unsaturated fatty acids in a living organism and various oxidation reactions always take place therein, the production of various peroxides of these unsaturated fatty acids is naturally expected. But there is no suitable method for measuring lipoperoxides in a living organism or in a living sample, so that the amount of lipoperoxides present under physiological conditions and turnover time are quite unknown yet, although the lipoperoxides have been discussed as causative agents for dysfunction and degeneration of material in a living organism. Further, lipoperoxides may naturally change in a tissue and sometimes seems to appear in a living sample, for example, serum. Therefore, if the amount of lipoperoxides in a living sample can be determined easily and precisely, such a method will be very helpful for an investigation of causes of arteriosclerosis and a remedy thereof.

On the other hand, peroxidic substances can also be present in fats and oils, processed foodstuffs from fats and oils, organic compounds easily oxidized to produce peroxidic substances such as ethers as undesirable impurities, which are produced mainly as hydroperoxides at high temperatures, or by irradiation of light, or in the presence of trace amounts of metals. In fats and oils or processed foodstuffs from fats and oils, hydroperoxides thus produced and accumulated gradually decompose to so-called secondary products containing aldehydes and acids, which cause degeneration and deterioration. In ethers, hydroperoxides thus produced cause a danger of explosion or unexpected reactions when used as solvent in chemical reactions.

Lipids are always subjected to autoxidation in a living organism and the resulting lipoperoxides are also changeable and unstable. On the other hand, fats and oils, processed foodstuffs from fats and oils and ethers are also subjected to autoxidation to produce hydroperoxides. But there has been no established method for determining trace amounts of peroxidic substances in a sample, living or non-living, although various methods have been proposed; for example, the following methods are disclosed in "Rinsho Kagaku" (Clinical Chemistry) vol. 1, pages 52-63, 1971:

1. Direct methods for measuring hydroperoxides
   (1) Iodine method
   (2) Iron thiocyanate method
   (3) Ultraviolet absorption spectrum method
2. Indirect method
   (1) Thiobarbituric acid method As to the iodine method, it is possible to measure a large amount of peroxidic substances in fats and oils as peroxide values using an iodine titration method in the chemistry of fats and oils employing very strict reaction conditions, but said method is not suitable for measuring a large number of samples due to complicated procedures. On the other hand, in the field of clinical chemistry, it is impossible to practice the iodine method for measuring trace amounts of lipoperoxides using a very small amount of living sample such as human blood.

The only one method presently used in clinical medicine is the thiobarbituric acid method wherein malondialdehyde produced secondarily from lipoperoxides by heating in acidic conditions is reacted with thiobarbituric acid to produce a red color compound, which is determined colorimetrically or fluorimetrically. In such a case, however, there is a coexisting substance which shows a similar reaction with thiobarbituric acid in the living sample other than the lipoperoxides. Such a coexisting substance should be removed before the determination by complicated procedures, for example, precipitating and separating the lipoperoxides together with proteins, subsequently removing an interfering substance such as glucose by washing to react only the lipoperoxides with thiobarbituric acid, and if necessary the resulting reaction products may be extracted with a solvent. Further in the thiobarbituric acid method, peroxides of unsaturated fatty acids having at most two double bonds such as linolic acid are negative in the reaction with thiobarbituric acid and the substance to be measured is not the lipoperoxides themselves but the malondialdehyde precursor produced by the peroxidation of the lipids. Moreover, the measured values varies widely depending on the separation conditions of the lipids and pH conditions or the amount of coexisting proteins in the procedure of removing the proteins and degree of coloring of a standard malondialdehyde is not always constant under the same conditions. Therefore, it is recommended that mutual comparison of data measured should be limited to those obtained under the strictly identical conditions ("Taisha" (Metabolism), vol. 13, 153, 1976). The thiobarbituric acid method is not suitable for determining peroxidic substances in fats and oils, and other organic materials since the peroxidic substances are not directly measured and there are some problems in degree of precision of the values measured.

Since the above-mentioned methods are principally insufficient for applying to the determination of peroxidic substances in a sample or to clinical examinations or too complicated to apply to daily examinations, a simple and precise method for measuring the amount of peroxidic substance in a sample, living or non-living, has long been desired.

It is an object of this invention to provide a method for measuring the amount of peroxidic substances in a sample, living or non-living, colorimetrically with a simple and precise procedure.

This invention provides a method for determining one or more peroxidic substances in a sample which comprises contacting the peroxidic substances with an oxidizable color reagent in the presence of a metallic compound produced from a metal which is able to have two or more valences to produce color, and measuring degree of coloring.

The method of this invention is to measure the amount of one or more peroxidic substances in a living or non-living sample by using remarkably increased oxidizing ability of the peroxidic substances in the presence of a metallic compound produced from a metal which is able to have two or more valences. Since the peroxidic substances react with the oxidizable color reagent quantitatively and are colored in the presence of the special metallic compound, the amount of the peroxidic substances in the sample can be measured quantitatively by the method of this invention.

According to this invention, whole amount of the peroxidic substances present in the sample can be determined. Thus all the amounts of two or more peroxidic substances present in the sample can also be determined. Since the amount of malondialdehyde which is a secondarily decomposed product of peroxidic lipids is measured in the thiobarbituric acid method, the amount of a peroxidic substance which cannot produce malondialdehyde cannot be measured. On the contrary, in this invention, the amount of one or more peroxidic substances such as lipoperoxides (peroxide values) in the sample can be rapidly and precisely determined using remarkably simple and easy procedures with the following advantages; that is, it is not necessary to remove proteins during the operation, conventional oxidizable color reagents can be used, expensive reagents are not necessary, the amount of a sample to be measured can be reduced remarkably due to high detection sensitivity, this method can be applied not only to a hand method but also to autoanalysis, etc.

The term "peroxidic substance" means for example lipoperoxides, peroxides of palmitoleic, palmitic, oleic, elaidic, vaccenic, linoleic, linolenic, γ-linolenic, eleostearic, arachidonic, clupanodonic acids or their esters such as glycerin esters, cholesterol esters, etc., in a living sample hydroperoxides, etc. present in fats and oils or ethers.

The peroxidic substances can be reacted with the oxidizable color reagent in a sample as it is. When the peroxidic substances are lipoperoxides, it is preferable to extract the lipoperoxides from a living sample with a solvent before the color producing reaction. As the solvent, an organic solvent is preferable in order to remove caeruloplasmin, or the like from the system. Examples of the organic solvents are hydrocarbons such as hexane, etc., alcohols such as methanol, ethanol, propanol, isopropanol, butanol, etc., halogenated hydrocarbons such as chloroform, carbon tetrachloride, etc., dimethylformamide (DMF), dimethylsulfoxide (DMSO), N-methyl-pyrrolidone, etc. These solvents can be used alone or as a mixture of two or more of them.

Extraction percentage of lipoperoxides by using a solvent such as an organic solvent is very good. For example, 200 μl of human serum is placed in a test tube and 4 ml of isopropyl alcohol is added thereto and mixed with stirring. The resulting mixture is centrifuged and 3 ml of supernatant liquid is taken out and concentrations of triglycerides, cholesterol, phospholipids and free fatty acids are measured according to conventional methods. Extraction percentages of these lipoperoxides to the isopropyl alcohol are as follows:

| | Concentration in serum (mg/l) | Extraction percentage (%) |
|---|---|---|
| Triglycerides | 112 | 96.7 |
| | 183 | 93.7 |
| Cholesterol | 151 | 94.7 |
| | 188 | 91.0 |
| Phospholipids | 254 | 90.3 |
| | 179 | 88.1 |
| Free fatty acids | 0.25 meq/l | 83.2 |

-continued

| | Concentration in serum (mg/l) | Extraction percentage (%) |
|---|---|---|
| | 0.49 meq/l | 88.7 |

In the case of the extraction with a solvent, even if metallic compounds produced from metals which are able to have two or more valences are present in a living sample, for example, serum, blood plasma, blood, they are not extracted together with lipoperoxides.

Such an organic solvent may contain an oxidizable color reagent, or one component of the combined oxidizable color reagent system as will be explained hereinafter.

The lipoperoxides extracted with such an organic solvent is then reacted with an oxidizable color reagent in the presence of a metallic compound produced from a metal which is able to have two or more valences in the solvent used for the extraction.

If necessary, the lipoperoxides in a living sample may be precipitated by a removing agent for proteins such as trichloroacetic acid together with the proteins and extracted with a solvent from the precipitate. In such a case, specificity and selectivity for measuring the lipoperoxides can further be increased remarkably.

As the living sample, serum, blood plasma, or blood of human beings or other animals can be used. The amount of the living sample used is usually about 5 to 500 μl.

In the case of using a non-living sample such as a sample of fats and oils, processed foodstuffs made from fats and oils, and organic compounds easily oxidizable to produce peroxidic substances such as ethers, about 5 to 50 μl of a sample is usually used. It is preferable to use a solvent to produce a uniform sample solution with such a sample as fats and oils, or the like. About 0.1 to 1 ml of the sample solution is usually used for the measurement. Examples of the solvents are organic solvents such as alcohols, e.g. methyl alcohol, ethyl alcohol, propyl alcohol, isopropyl alcohol, butyl alcohol, etc., ketones, e.g. acetone, methyl ethyl ketone, etc., Cellosolve, e.g. methyl Cellosolve, ethyl Cellosolve, etc., dimethylsulfoxide, dimethylformamide; or a mixture of one or more of these solvents with a halogenated hydrocarbon such as carbon tetrachloride, chloroform, or the like, or a hydrocarbon such as hexane, heptane, or the like. Among them, a mixture of an alcohol such as ethyl alcohol with a halogenated hydrocarbon such as carbon tetrachloride is preferable from the viewpoint of stability of a sample solution and stability of a color producing solution, since such a solvent can also be used together with an oxidizable color reagent to produce a color producing solution.

The color production (or development) is carried out by contacting or reacting the peroxidic substances in the sample or in an organic solvent with which the peroxidic substances have been extracted with the oxidizable color reagent in the presence of a metallic compound produced from a metal which is able to have two or more valences. When human serum is used as a living sample, the specific metallic compound produced from a metal which is able to have two or more valences such as iron compounds and copper compounds are already present in the living sample in a considerable amount, so that it is not always necessary to add the metallic compound to the living sample. But, it is preferable to add the specific metallic compound to the living sample in order to accelerate the reaction rate for producing color, to shorten the reaction time, and to raise detection sensitivity. When a living or non-living sample does not contain or contains an insufficiently small amount of a metallic compound produced from a metal which is able to have two or more valences, it is necessary to add such a metallic compound to the sample so as to make the metallic compound present therein sufficiently. Preferable amount of the metallic compound in the sample is about $1\times10^{-6}$ to $1\times10^{-1}$% by weight.

The metallic compound produced from a metal which is able to have two or more valences is usually soluble in water or the like solvent, but not limited to it, and further even dissolved in the solvent, it is not limited to one which ionizes. Typical examples of these metallic compounds are transition metal compounds, but the metal contained therein is not limited to the transition metals. Examples of the metals which are able to have two or more valences are transition metals belonging to Period 4 of the periodic table such as titanium, vanadium, manganese, iron, nickel, copper, etc.; transition metals belonging to Period 5 of the periodic table such as molybdenum, etc.; transition metals belonging to Period 6 of the periodic table such as lanthanum series metals, e.g. cerium, etc., and tungsten, etc.; transition metals of actinium series, thallium, etc.

The compounds containing these metals are usually dissolved in water but it is not certain whether the metals are present in the form of ions or not. Even if they are present in the form of ions, they are effective. Examples of these ions are vanadium ions, vanadate ions, metavanadate ions, manganese ions, iron ions, ferricyanide ions, ferrocyanide ions, iron complex ions, cobalt ions, nickel ions, copper ions, copper complex ions, molybdate ions, phosphomolybdate ions, cerium ions, tungstate ions, thallium ions, etc. In order to obtain these ions, there can be used salts, complex salts, double salts or water-soluble compounds which can produce cations or anions of these ions usually dissolved in water. It is preferable to coexist molybdate or tungstate ions with iodine ions. As examples of iron complex salts, not only ferricyanide ions and ferrocyanide ions but also heme, i.e. iron-porphyrin complex, can also effectively be used. The metallic compounds can be added to the sample or to the extracted sample solution to be measured singly or as a mixture of two or more of them.

As the oxidizable color reagents, any conventional ones which can produce color when oxidized can be used, since oxidation ability of the peroxidic substances such as lipoperoxides in the sample or the extracted sample solution is remarkably enhanced in the presence of the metallic compound produced from the metal which is able to have two or more valences. Examples of the oxidizable color reagents are N,N-dialkyl-p-phenylenediamine such as N,N-dimethyl-p-phenylenediamine, N,N-diethyl-p-phenylenediamine, etc., N-alkyl-N-hydroxyalkyl-p-phenylenediamine such as N-ethyl-N-hydroxyethyl-p-phenylenediamine, etc., N,N-bis(hydroxyalkyl)-p-phenylenediamine such as N,N-bis(hydroxymethyl)-p-phenylenediamine, etc., 4-amino-3-alkyl-N,N-dialkylaniline such as 4-amino-3-methyl-N,N-dimethylaniline, 4-amino-3-methyl-N,N-diethylaniline, etc., 4-amino-3-alkyl-N-alkyl-N-hydroxyalkylaniline such as 4-amino-3-methyl-N-methyl-N-($\beta$-hydroxyethyl)aniline, 4-amino-3-methyl-N-ethyl-N-($\beta$-hydroxyethyl)aniline, etc., 4-amino-3-alkyl-N,N-bis(hydroxyalkyl)aniline such as 4-amino-3-methyl-N,N-bis(-hydroxyethyl)aniline, etc., 4-amino-2-alkyl-N,N-dialkylaniline such as 4-amino-2-methyl-N,N-diethylaniline, etc., 4-amino-2-alkyl-N-alkyl-N-hydroxyalkylaniline such as 4-amino-2-methyl-N-ethyl-N-hydroxyethylaniline, etc., 4-amino-2-alkyl-N,N-bis(hydroxyalkyl)aniline such as 4-amino-2-methyl-N,N-bis(hydroxyethyl)aniline, etc., 4-amino-3-alkyl-N-alkyl-N-alkanesulfonamidealkylaniline such as 4-amino-3-methyl-N-methyl-N-($\beta$-methanesulfonamidethyl)aniline, 4-amino-3-methyl-N-ethyl-N-($\beta$-methanesulfonamidethyl)aniline, etc., 4-amino-2-alkyl-N-alkyl-N-alkanesulfonamidealkylaniline such as 4-amino-2-methyl-N-propyl-N-methanesulfonamidoethylaniline, etc. In addition to substituted p-phenylenediamines such as N-substituted-p-phenylenediamines and their nuclear substitution derivatives mentioned above there can also be used benzidine and its alkyl or alkoxy nuclear substitution compounds such as o-tolidine, bianisidine, etc., indole and its derivatives, 2,2'-azino-bis(3-alkylbenzothiazoline-6-sulfonic acid) such as 2,2'-azino-bis(3-methylbenzothiazoline-6-sulfonic acid), 2,2'-azino-bis(3-ethylbenzothiazoline-6-sulfonic acid), etc.

As the oxidizable color reagents, a combination of 4-amino-antipyrine or 3-alkyl-2-benzothiazolinonehydrazone as one component and a substituted aniline such as a N-substituted aniline or its nuclear substitution derivative as another component can also preferably be used. Examples of 3-alkyl-2-benzothiazolinonehydrazones are 3-methyl-2-benzothiazolinonehydrazone, etc. Examples of substituted anilines are N,N-dialkylaniline such as N,N-dimethylaniline, N,N-diethylaniline, etc., 3-alkyl-N,N-dialkylaniline such as 3-methyl-N,N-dimethyl aniline, 3-methyl-N,N-diethylaniline, etc., 2-alkyl-N,N-dialkylaniline such as 2-methyl-N,N-diethylaniline, etc., N-alkyl-N-hydroxyalkylaniline such as N-methyl-N-($\beta$-hydroxyethyl)aniline, N-ethyl-N-($\beta$-hydroxyethyl)aniline, etc., 3-alkyl-N-alkyl-N-hydroxyalkylaniline such as 3-methyl-N-methyl-N-($\beta$-hydroxyethyl)aniline, 3-methyl-N-ethyl-N-($\beta$-hydroxyethyl-)aniline, etc., 2-alkyl-N-alkyl-N-hydroxyalkylaniline such as 2-methyl-N-ethyl-N-hydroxyethylaniline, etc., N,N-bis(hydroxyalkyl)aniline such as N,N-bis(hydroxyethyl)aniline, etc., 3-alkyl-N,N-bis(hydroxyalkyl)aniline such as 3-methyl-N,N-bis(hydroxyethyl)aniline, etc., 2-alkyl-N,N-bis(hydroxyalkyl)aniline such as 2-methyl-N,N-bis(hydroxyethyl)aniline, etc., 3-alkyl-N-alkanesulfonamidealkylaniline such as 3-methyl-N-methyl-N-($\beta$-methanesulfonamideethyl)aniline, 3-methyl-N-ethyl-N-($\beta$-methanesulfonamidoethyl)aniline, etc., 2-alkyl-N-alkyl-N-alkanesulfonamidoalkylaniline such as 2-methyl-N-propyl-N-methanesulfonamidoethylaniline, etc.

In the case of non-living samples such as fats and oils, processed foodstuffs produced therefrom, and ethers, it is preferable to use as the oxidizable color reagent a mixture of a 3-alkyl-2-benzothiazolinonehydrazone with an aniline derivative of the formula:

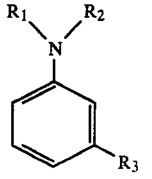

(I)

wherein $R_1$ and $R_2$ are independently alkyl having 1 to 5 carbon atoms or hydroxyalkyl having 1 to 5 carbon atoms; and $R_3$ is hydrogen or alkyl having 1 to 5 carbon atoms, or a mixture of 4-aminoantipyrine with an aniline derivative of the formula (I) mentioned above, or an aniline derivative of the formula:

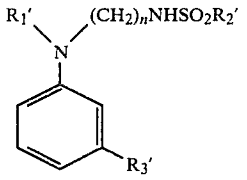

(II)

wherein $R'_1$, $R'_2$ and $R'_3$ are alkyl having 1 to 5 carbon atoms; and n is an integer of 1 to 3.

In place of the combined use of 4-aminoantipyrine and an aniline derivative, reaction products of 4-aminoantipyrine and an aniline derivative can be used. Such reaction products are novel compounds having the formula:

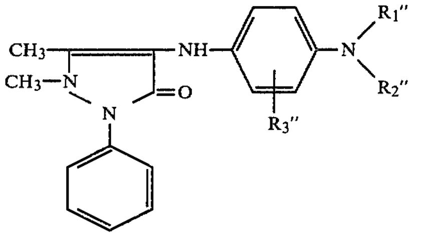

(III)

wherein $R''_1$ and $R''_2$ are independently hydrogen, $C_{1-3}$ alkyl, hydroxy $C_{1-3}$ alkyl or phenyl; and $R''_3$ is hydrogen, $C_{1-3}$ alkyl, sulfo, or a group of the formula $X-OSO_2-$ in which X is an alkali metal, alkaline earth metal or $NH_4-$. The term "$C_{1-3}$ alkyl" includes methyl, ethyl, propyl, etc. The term "hydroxy-$C_{1-3}$ alkyl" includes hydroxymethyl, hydroxyethyl, hydroxypropyl, etc.

The compound of the formula (III) can be produced, for example, as follows:

4-Aminoantipyrine and an aniline derivative are dissolved in diluted hydrochloric acid and a metaperiodate is added thereto dropwise under ice cooling and after the dropwise addition, the resulting mixture is stirred at room temperature for about 1 hour. 4-Aminoantipyrine and the aniline derivative are subjected to oxidative condensation to produce a quinone coloring matter. When a saturated sodium chloride aqueous solution or the like is added to this reaction solution, crystals are deposited. After collecting the crystals by filtration, the crystals are dissolved in acetone and hydrosulfite is added thereto to conduct reduction until the solution is discolored. After removing the acetone by distillation, the desired compound of the formula (III) can be filtered off as crystals.

Examples of the aniline derivatives are N,N-dimethylaniline, N,N-diethylaniline, N,N-dipropylaniline, diphenylamine, o-aminobenzenesulfonic acid, N-ethyl-N-hydroxyethyl-m-toluidine, and the like.

Examples of the compounds of the formula (III) are as follows:

4-(p-Dimethylaminoanilino)antipyrine, m.p. 208.5°-209.0° C. (decomposed):

Elementary analysis (%):

| | H | C | N |
|---|---|---|---|
| Calculated | 6.88 | 70.78 | 17.38 |
| Found | 7.04 | 70.65 | 17.38 |

4-(p-Diethylaminoanilino)antipyrine, m.p. 208.0°-209.5° C. (decomposed):

Elementary analysis (%):

| | H | C | N |
|---|---|---|---|
| Calculated | 7.48 | 71.96 | 15.99 |
| Found | 7.51 | 72.00 | 15.88 |

4-(p-Di-n-propylaminoanilino)antipyrine, m.p. 210.0°-212.0° C. (decomposed):

Elementary analysis (%):

| | H | C | N |
|---|---|---|---|
| Calculated | 7.99 | 72.98 | 14.81 |
| Found | 8.06 | 72.97 | 14.96 |

4-(p-Phenylaminoanilino)antipyrine, m.p. 233°-236° C. (decomposed):

Elementary analysis (%):

| | H | C | N |
|---|---|---|---|
| Calculated | 5.99 | 74.57 | 15.13 |
| Found | 5.84 | 74.68 | 15.09 |

4-(3'-Sulfo-4'-methylanilino)antipyrine, m.p. 236.0°-238.0° C. (decomposed):

Elementary analysis (%):

| | H | C | N |
|---|---|---|---|
| Calculated | 5.46 | 53.19 | 13.79 |
| Found | 5.25 | 53.08 | 13.64 |

4-(2'-Methyl-4'-N-ethyl-N-hydroxyethylaminoanilino)antipyrine, m.p. 210.0°-212.0° C. (decomposed):

Elementary analysis (%):

| | H | C | N |
|---|---|---|---|
| Calculated | 7.99 | 72.98 | 14.81 |
| Found | 8.00 | 72.97 | 14.96 |

Further when a substituted p-phenylenediamine is used as the oxidizable color reagent, it is preferable to use said substituted p-phenylenediamine together with a coupler such as sodium 1-naphthol-5-sulfonate, sodium 1-naphthol-8-sulfonate, potassium 1-naphthol-2-sulfonate, 2,4-dichloro-1-naphthol, 1-(2',4',6'-trichlorophenyl)-3-(3'-nitrobenzoylamino)-2-pyrazoline-5-one, 1-(2',4',6'-trichlorophenyl)-3-(3'-aminobenzoylamino)-2-pyrazoline-5-one, 1-phenyl-3-amino-2-pyrazoline-5-one, 1-(2'-chlorophenyl)-3-amino-2-pyrazoline-5-one, etc.

The combined use of a 3-alkyl-2-benzothiazolinonehydrazone together with an aniline derivative shows about 3 to 4 times as effective as the combined use of 4-aminoantipyrine together with an aniline derivative for color producing (or color development)

and the former has an advantage in that it slightly influence on measured values of hemoglobin in hemolyzed serum.

The oxidizable color reagent is oxidized by the peroxide substances such as lipoperoxides in the sample or in the extracted sample solution in the presence of a metallic compound produced from a metal which is able to have two or more valences to produce color. Such a color producing reaction usually increases its reaction rate with and increase of the reaction temperature. The reaction temperature can be selected freely depending on an object of the reaction and not limited to a certain range, but it is preferable to carry out the reaction at about 37° C. when the amount of peroxidic substances such as lipoperoxides are to be determined from color producing rate. When the amount of peroxidic substances such lipoperoxides is to be determined from the point after some period of the reaction proceeded, a higher reaction temperature makes a measuring time shorter due to the increased reaction rate.

pH of the color producing reaction can be selected depending on a proper pH range of the oxidizable color reagent used for color development. In order to remarkably increase selectivity for measuring the hydroperoxides present in a living sample, it is preferable to treat the living sample at about pH 5 or less or at about pH 10 or more before or the same time as the color producing reaction, i.e. placing the sample under at about pH 5 or less or at about pH 10 or more at 10° C.-50° C. for a prescribed time. When lipoperoxides are extracted with a solvent and then the color producing reaction is carried out, it is not necessary to limit the pH of said reaction to such pH ranges as mentioned above. In the case of non-living samples such as fats and oils, such pH ranges as mentioned above are not necessary for the color producing reaction.

In order to adjust the pH of the reaction system properly, an acid, an alkali or a buffer solution can preferably be used. Examples of inorganic acids are hydrochloric acid, sulfuric acid, phosphoric acid, etc; examples or organic acids are acetic acid, succinic acid, phthalic acid, etc; examples of inorganic alkalis are ammonia water, sodium carbonate, potassium carbonate, sodium hydroxide, potassium hydroxide, etc.; examples of buffer solutions are a phosphate buffer solution, an acetate buffer solution, a phthalate buffer solution, a glycine-hydrochloride buffer solution, a succinate buffer solution, a borate buffer solution, etc; and there can be used organic bases.

Degree of coloring thus produced can be measured by a conventional colorimetrical method. In the case of measuring absorbance, absorbance near a maximum absorption wavelength of the color produced is usually measured.

An mentioned above, according to the present invention, the peroxidic substances such as lipoperoxides in a living or non-living sample can be measured rapidly and precisely by using a remarkably simple procedure. The present invention is very effective for diagnosis of arteriosclerosis, diabetes mellitus, and the like diseases, and observation of the progress of remedy, and prevention of immature foetus retinopathy, and the like. Therefore, the method of the present invention can contribute to clinical medicine greatly.

The present invention is explained more in detail by way of the following Examples but not limited thereto.

EXAMPLES 1-33

A color developing solution A is prepared by mixing 100 ml of 0.1 M acetate buffer solution (pH 5.0) with an oxidizable color reagent of 28 mg (0.14 mmole) of 4-aminoantipyrine and 134 mg (0.8 mmole) of N-ethyl-N-hydroxyethyl-3-methylaniline.

A color developing solution B is prepared by dissolving 50 mg of anhydrous ferric chloride ($FeCl_3$) in 1 liter of distilled water.

In a test tube, 20 μl of human serum is placed and 3 ml of the color developing solution A and 0.1 ml of the color developing solution B are added to the test tube and mixed well. After allowing the test tube to stand in a constant temperature water bath set at 37° C. for 10 minutes, absorbance at 545 nm ($E_1$) is measured. After allowing the test tube to stand at 37° C. for 20 minutes, absorbance at 545 nm ($E_2$) is measured.

The same procedures as mentioned above are repeated for distilled water in place of the serum sample to measure absorbance at 545 nm, $E_{B1}$ and $E_{B2}$. Absorbance of the sample is obtained by calculating the following equation:

$$\text{Absorbance of sample } (\Delta E_s) = (E_2 - E_1) - (E_{B2} - E_{B1})$$

The same procedures as mentioned above are repeated for a standard sample to give absorbance of the standard sample ($\Delta E_{std}$). Peroxide value of the sample is obtained from the following equation:

$$\text{Peroxide value of the sample} = \frac{\Delta E_s}{\Delta E_{std}} \times \left(\text{Peroxide value of the standard sample}\right)$$

Since human serum contains 1200 μg of iron and 1000 μg of coper per 1 liter, color is clearly produced by adding only the color developing solution A and not adding color developing solution B (Example 1).

To human serum, hydrochloric acid and trichloroacetic acid are added to precipitate proteins. The precipitate is separated from a supernatant liquid by centrifugation. When the precipitate is dissolved in water to give a sample solution and only the color developing solution A is added thereto, no color is developed as shown in Comparative Example, whereas when both the color developing solutions A and B are added to the sample solution, there takes place color development (Examples 2-17).

In the case of Example 1, since human serum contains peroxidic substances together with iron and copper compounds, it has sufficient ability for oxidizing the oxidizable color reagent. On the other hand, in the case of Comparative Example, the sample solution obtained from the precipitated proteins contains no metallic compound produced from a metal which is able to have two or more valences such as iron and copper compounds therein, the lipoperoxides in the precipitate have no sufficient ability to oxidize the oxidizable color reagent and thus no color development takes place. When a metallic compound produced from a metal which is able to have two or more valences is added to the sample solution as shown in Examples 2-17, the peroxidic substances included in the precipitate become to be able to have sufficient ability to oxidize the oxidizable color reagent so as to develop color.

The above mentioned results are shown in Table 1, wherein oxidizing ability of the peroxidic substances (degree of coloring) is also listed.

TABLE 1

| Example No. | Metallic compound: Compound | Metal contained in the compound | Amount (w/v %) | Oxidizing ability of peroxidic substances |
|---|---|---|---|---|
| 1 | Metal compounds contained in human serum | Fe ... 1200 μg/l<br>Cu ... 1000 μg/l | | Yes (+) |
| 2 | $FeCl_3$ | $Fe(Fe^{3+})$ | 0.002 | Yes (+) |
| 3 | $FeCl_3$ | $Fe(Fe^{3+})$ | 0.0007 | Yes (+) |
| 4 | $FeCl_3$ | $Fe(Fe^{3+})$ | 0.0003 | Yes (+) |
| 5 | $FeSO_4(NH_4)_2SO_4$ | $Fe(Fe^{2+})$ | 0.01 | Yes (+) |
| 6 | $(CH_3COO)_2Cu$ | $Cu(Cu^{2+})$ | 0.003 | Yes (+) |
| 7 | $(CH_3COO)_2Cu$ | $Cu(Cu^{2+})$ | 0.0003 | Yes (+) |
| 8 | $(CH_3COO)_2Mn$ | $Mn(Mn^{2+})$ | 0.003 | Yes (+) |
| 9 | $(CH_3COO)_3Ce$ | $Ce(Ce^{3+})$ | 0.007 | Yes (+) |
| 10 | $(CH_3COO)_3Ce$ | $Ce(Ce^{3+})$ | 0.003 | Yes (+) |
| 11 | $NiCl_2$ | $Ni(Ni^{2+})$ | 0.003 | Yes (+) |
| 12 | $(CH_3COO)_2Co$ | $Co(Co^{2+})$ | 0.007 | Yes (+) |
| 13 | $(CH_3COO)_2Co$ | $Co(Co^{2+})$ | 0.003 | Yes (+) |
| 14 | $NaMoO_4$ | $Mo(MoO_4^-)$ | 0.003 | Yes (+) |
| 15 | $NaWO_4$ | $W(WO_4^-)$ | 0.003 | Yes (+) |
| 16 | $NH_4VO_3$ | $V(VO_3^-)$ | 0.003 | Yes (+) |
| 17 | VO-acetylacetone salt | V(VO) | 0.003 | Yes (+) |
| Comparative Example | None | | | No (−) |

In the next place, both the color developing solutions A and B are added directly to human serum samples (containing 1200 μg of iron and 1000 μg of copper per liter) (Examples 18–33) to develope color as mentioned above and relationship between oxidizing ability of peroxidic substances when metallic compounds produced from the metal which is able to have two or more valences are added thereto and that of Example 1 wherein the metallic compounds are present in the serum sample inherently is compared. The results are as shown in Table 2. In Table 2, degree of coloring (absorbance of the sample) of Example 1 is taken as 1.00 and ratios of degree of coloring of individual samples of Examples 18–33 to degree of coloring of Example 1 are used for showing oxidizing ability of peroxidic substances (degree of coloring).

TABLE 2

| Ex. No. | Metallic compound: Compound | Metal contained in the compound | Amount of added (w/v %) | Oxidizing ability of peroxidic substance (ratio) |
|---|---|---|---|---|
| 1 | Metal compounds contained in human serum | Fe ... 1200 μg/l<br>Cu ... 1000 μg/l | | 1.00 |
| 18 | $FeCl_3$ | $Fe(Fe^{3+})$ | 0.002 | 12.20 |
| 19 | $FeCl_3$ | $Fe(Fe^{3+})$ | 0.0007 | 12.08 |
| 20 | $FeCl_3$ | $Fe(Fe^{3+})$ | 0.0003 | 11.36 |
| 21 | $FeSO_4(NH_4)_2SO_4$ | $Fe(Fe^{2+})$ | 0.002 | 13.70 |
| 22 | $(CH_3COO)_2Cu$ | $Cu(Cu^{2+})$ | 0.003 | 10.64 |
| 23 | $(CH_3COO)_2Cu$ | $Cu(Cu^{2+})$ | 0.0003 | 3.20 |
| 24 | $(CH_3COO)_2Mn$ | $Mn(Mn^{2+})$ | 0.003 | 1.09 |
| 25 | $(CH_3COO)_3Ce$ | $Ce(Ce^{3+})$ | 0.007 | 1.48 |
| 26 | $(CH_3COO)_3Ce$ | $Ce(Ce^{3+})$ | 0.003 | 1.03 |
| 27 | $NiCl_2$ | $Ni(Ni^{2+})$ | 0.003 | 1.66 |
| 28 | $(CH_3COO)_2Co$ | $Co(Co^{2+})$ | 0.007 | 1.48 |
| 29 | $(CH_3COO)_2Co$ | $Co(Co^{2+})$ | 0.003 | 1.05 |
| 30 | $NaMoO_4$ | $Mo(MoO_4^-$ | 0.003 | 1.10 |
| 31 | $NaWO_4$ | $W(WO_4^-$ | 0.003 | 1.28 |
| 32 | $NH_4VO_3$ | $V(VO_3^-$ | 0.003 | 6.12 |
| 33 | VO-acetylacetone salt | V(VO) | 0.003 | 1.85 |

As is clear from Table 2, even if there are the metallic compounds produced from metals which are able to have two or more valences in the sample inherently, said metallic compounds having sufficient ability for oxidizing the oxidizable color reagent, addition of further metallic compounds produced from metals which are able to have two more valences to the samples makes the oxidizing ability of peroxidic substances increase. These effects are remarkable when compounds of iron, copper and vanadium are added.

EXAMPLES 34–44

A color developing solution is prepared by mixing 1 liter of 0.05 M acetate buffer solution (pH 5.0) with 1.48 mmole of 4-aminoantipyrine and 8.4 mmole of a substituted aniline as listed in Table 3 as an oxidizable color reagent.

To 50 μl of human serum sample (Fe 1200 μg/l, Cu 1050 μg/l), 3.0 ml of the color developing solution is added and the resulting mixture is allowed to stand at 37° C. in a constant temperature water bath for 10 minutes. Subsequently, absorbance at a maximum absorption wavelength ($E_1$) is measured. Then the mixture is allowed to stand at 37° C. for further 20 minutes to measure absorbance at the maximum absorption wavelength ($E_2$).

The same procedures as mentioned above are repeated for distilled water in place of the serum sample to measure absorbance $E_{B1}$ and $E_{B2}$. Degree of coloring is obtained from the following equation:

$$\text{Degree of coloring (Absorbance of sample)} = (E_2 - E_1) - (E_{B2} - E_{B1})$$

The results are as shown in Table 3, wherein degree of coloring in Example 34 is taken as 1.00 and ratios of each value to that of Example 34 are shown in Table 3 as degree of coloring.

TABLE 3

| Example No. | Oxidizable color reagent | Substituted aniline | Maximum absorption wave length (nm) | Degree of coloring (ratio) |
|---|---|---|---|---|
| 34 | 4-Amino-antipyrine | N-Ethyl-N-hydroxyethyl-3-methylaniline | 545 | 1.00 |
| 35 | 4-Amino-antipyrine | N,N-Diethyl-3-methylaniline | 545 | 0.54 |
| 36 | 4-Amino- | N-Methyl-N-hydroxyethyl-3- | | |

TABLE 3-continued

| Example No. | Oxidizable color reagent | | Maximum absorption wave length (nm) | Degree of coloring (ratio) |
|---|---|---|---|---|
| | | Substituted aniline | | |
| | antipyrine | methylaniline | 545 | 1.10 |
| 37 | 4-Amino-antipyrine | N,N-Dimethyl-3-methylaniline | 545 | 0.93 |
| 38 | 4-Amino-antipyrine | N,N-Bis(β-hydroxyethyl)-3-methylaniline | 567 | 1.20 |
| 39 | 4-Amino-antipyrine | N,N-Dimethylaniline | 545 | 1.02 |
| 40 | 4-Amino-antipyrine | N,N-Diethylaniline | 545 | 0.65 |
| 41 | 4-Amino-antipyrine | N,N-Bis(β-hydroxyethyl)-aniline | 567 | 1.05 |
| 42 | 4-Amino-antipyrine | N-Ethyl-N-hydroxyethylaniline | 545 | 0.87 |
| 43 | 4-Amino-antipyrine | N-Ethyl-N-(β-methanesulfonamido-ethyl)-3-methylaniline | 545 | 0.90 |
| 44 | 4-Amino-antipyrine | N-Methyl-N-(β-methanesulfonamido-ethyl)-3-methylaniline | 545 | 1.05 |

EXAMPLE 45

A color developing solution is prepared by mixing 100 ml of 1.0 M acetate buffer solution (pH 5.0) with 33 mg of 4-aminoantipyrine (0.16 mmole) and 145 mg of a substituted aniline as listed in Table 4 (0.8 mmole) as an oxidizable color reagent.

To 50 μl of human serum sample, 3 ml of the color developing solution is added and mixed and the resulting mixture is allowed to stand at 37° C. in a constant temperature water bath for 10 minutes. Subsequently 1 ml of 0.1 M carbonate buffer solution (pH 10.0) is added to the mixture and absorbance at 567 nm ($E_s$) is measured within 10 minutes.

The same procedure as mentioned above is repeated for distilled water in place of the serum sample to measure absorbance at 567 nm ($E_{BL}$). Absorbance of the sample is obtained from the following equation:

$$\text{Absorbance of sample} = E_s - E_{BL}$$

The same procedures as mentioned above are repeated for 50 μl of a standard sample to give absorbance of the standard sample. Peroxide value of the sample is obtained in the same manner as described in Example 1.

EXAMPLE 46

A color developing solution A is prepared by dissolving in 100 ml of 1.0 M acetate buffer solution (pH 5.0) or 0.1 M succinate buffer solution (pH 3.0) 31 mg (0.15 mmole) of 4-aminoantipyrine and 134 mg (0.8 mmole) of a substituted aniline as listed in Table 4 as an oxidizable color reagent.

A color developing solution B is prepared by dissolving 0.1 g of $FeCl_3$ in 1 liter of distilled water.

In a test tube, 10 μl or 200 μl of a sample (human serum) is placed and 3 ml of the color developing solution A and 0.1 ml of the color developing solution B are added to the test tube and mixed well. The mixture is allowed to stand at 37° C. in a constant temperature water bath for 30 minutes and absorbance at 545 nm ($E_s$) is measured.

The same procedure as mentioned above is repeated for distilled water in place of the sample to measure absorbance at 545 nm ($E_{BL}$).

The same procedure as mentioned above is repeated for 10 μl of a standard sample to give absorbance of the standard sample at 545 nm ($E_{std}$).

Peroxide value of the sample is obtained from the following equation:

$$\text{Peroxide value of the sample} = \frac{E_s - E_{BL}}{E_{std} - E_{BL}} \times \left(\text{Peroxide value of the standard sample}\right)$$

EXAMPLE 47

A color developing solution is prepared by dissolving 20 mg (0.1 mmole) of 4-aminoantipyrine and 73 mg (0.6 mmole) of a substituted aniline as listed in Table 4 in 100 ml of 0.1 M phosphate buffer solution (pH 5.0) or 0.1 M succinate buffer solution (pH 3.0) and adding 3 mg (0.025 mmole) of $NH_4VO_3$ thereto.

In a test tube, 20 μl or 300 μl of a sample (human blood plasma) is placed and 3.0 ml of the color developing solution is added to the test tube. The resulting mixture is allowed to stand at 50° C. in a constant temperature water bath for 10 minutes and absorbance at 545 nm ($E_s$) is measured.

The same procedure as mentioned above is repeated for distilled water in place of the sample to measure absorbance at 545 nm ($E_{BL}$). Absorbance of the sample is obtained from the following equation:

$$\text{Absorbance of sample} = E_s - E_{BL}$$

The same procedures as mentioned above are repeated for 20 μl of a standard sample to give absorbance of the standard sample at 545 nm. Peroxide value of the sample is obtained in the same manner as described in Example 46.

EXAMPLE 48

A color developing solution A is prepared by dissolving 31 mg (0.15 mmole) of 4-aminoantipyrine in 100 ml of 0.05 M acetate buffer solution (pH 5.0).

A color developing solution B is prepared by dissolving 179 mg (0.7 mmole) of a substituted aniline as listed in Table 4 in 100 ml of 0.05 M acetate buffer solution (pH 5.0).

Using an autoanalyzing machine (Kurinarizer H type, manufactured by Japan Electron Optics Laboratory Co., Ltd.) and a human serum or blood plasma sample as a living sample, absorbance is measured by the following procedure;

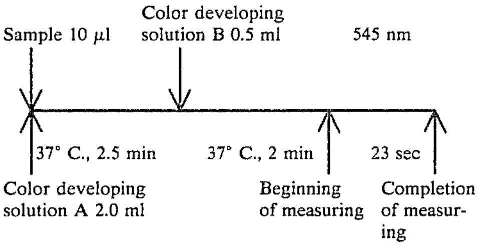

The same procedure as mentioned above is repeated for a standard sample to measure absorbance of the standard sample. Peroxide value of the sample is obtained by using factors determined based on the measured values of the standard sample.

EXAMPLE 49

A color developing solution is prepared by mixing 70 ml of 0.05 M acetate buffer solution (pH 5.0), and 30 ml of dimethylsulfoxide (DMSO) and dissolving 35 mg (0.17 mmole) of 4-aminoantipyrine and 167 mg (1.0 mmole) of the substituted aniline as listed in Table 4 therein.

In a test tube, 20 μl of a sample (human serum) is placed, and 3.0 ml of the color developing solution preheated at 37° C. is added to the test tube. Absorbance of the sample is recorded automatically at 37° C. for 10 minutes using a spectrophotometer (Hitachi 200-10 type) equipped with a constant temperature bath and an automatic recorder.

The same procedure as mentioned above is repeated for a standard sample and absorbance is recorded on recording paper for 10 minutes. Peroxide value of the sample is obtained by the ratio of absorbance of the sample to absorbance of the standard sample read from changes of absorbance for a period of 5 minutes from 5 to 10 minutes from the beginning of the recording.

EXAMPLE 50

A color developing solution A is prepared by dissolving 31 mg (0.15 mmole) of 4-aminoantipyrine and 134 mg (0.8 mmole) of the substituted aniline as listed in Table 4 in 100 ml of 0.5 M acetate buffer solution (pH 5.0).

A color developing solution B is prepared by dissolving 200 mg (1 mmole) of copper acetate in 1000 ml of 0.5 M acetate buffer solution (pH 5.0).

In a test tube, 20 μl of a sample (human serum) is placed, and 3 ml of the color developing solution A and 0.1 ml of the color developing solution B are added to the test tube and mixed. The mixture is allowed to stand at 37° C. in a constant temperature water bath for 10 minutes and absorbance at 545 nm ($E_1$) is measured. Then the mixture is allowed to stand at 37° C. for further 20 minutes and absorbance at 545 nm is measured ($E_2$).

The same procedures as mentioned above are repeated for distilled water in place of the serum sample to measure absorbance at 545 nm, $E_{B1}$ and $E_{B2}$. Absorbance of the sample is obtained from the following equation:

$$\text{Absorbance of sample} = (E_2 - E_1) - (E_{B2} - E_{B1})$$

The same procedures as mentioned above are repeated for 20 μl of a standard sample to obtain absorbance of the standard sample. Peroxide value of the sample is obtained from the ratio of absorbance of the sample to absorbance of the standard sample.

The substituted anilines, samples and metallic compounds used in Examples 45–50 are as listed in Table 4.

TABLE 4

| Example No. | Sample | Substituted aniline | Metallic compound added | Note |
|---|---|---|---|---|
| 45 | Human serum | 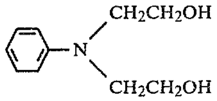 | None | Hand method |
| 46 | Human serum | 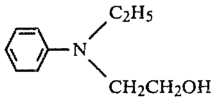 | $FeCl_3$ | Hand method (The end method) |
| 47 | Blood plasma | 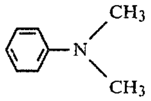 | $NH_4VO_3$ | Hand method |
| 48 | Blood plasma or Human serum | 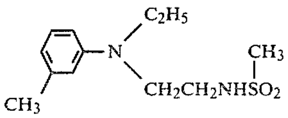 | None | Autoanalysis (Rate method) |
| 49 | Human serum | 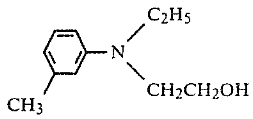 | None | Hand method |

TABLE 4-continued

| Example No. | Sample | Substituted aniline | Metallic compound added | Note |
|---|---|---|---|---|
| 50 | Human serum | 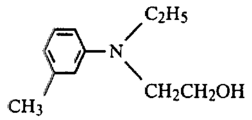 | $(CH_3COO)_2Cu$ | Hand method |

Note
Individual samples contain Fe 1160 μg/l and Cu 1100 μg/l.

EXAMPLE 51

A color developing solution is prepared by dissolving 90 mg (0.28 mmole) of 3-methyl-2-benzothiazolinonehydrazone and 234 mg (1.4 mmole) of N-ethyl-N-(β-hydroxyethyl)-3-methylaniline in 100 ml of 0.5 M acetate buffer solution (pH 5.0).

In a test tube, 50 μl of human serum is placed and 1 ml of aqueous solution containing 0.001% by weight of ferric chloride ($FeCl_3$) and 2 ml of the color developing solution are added thereto. The mixture is allowed to stand at 37° C. in a constant temperature water bath for 30 minutes and absorbance at 585 nm is measured.

EXAMPLE 52

In a test tube, 50 μl of human serum (Fe 1150 μg/l, Cu 1080 μg/l) is placed and 3 ml of 0.1 M acetate buffer solution (pH 5.0) containing N,N-diethyl-p-phenylenediamine in proportion of 8.4 mmole/l is added thereto. The resulting mixture is allowed to stand at 37° C. in a constant temperature water bath for 30 minutes and absorbance at 515 nm is measured.

EXAMPLE 53

In a test tube, 50 μl of human serum (Fe 1210 μg/l, Cu 1080 μg/l) is placed and 3 ml of 0.1 M acetate buffer solution (pH 5.0) containing dianisidine in proportion of 8.4 mmole/l is added thereto. Using the same procedure as mentioned in Example 52, absorbance at 520 nm is measured.

EXAMPLE 54

The procedure of Example 53 is repeated except for using benzidine in place of dianisidine and absorbance at 450 nm is measured.

EXAMPLE 55

In a test tube, 50 μl of human serum (Fe 1200 μg/l, Cu 1030 μg/l) is placed and 3 ml of 0.1 M of acetate buffer solution (pH 5.0) containing N,N-diethyl-p-phenylenediamine in proportion of 8.4 mmole/l and sodium 1-naphthol-5-sulfonate in proportion of 1 mmole/l is added thereto. The resulting mixture is allowed to stand at 37° C. in a constant temperature water bath for 30 minutes and 1 ml of 1 N sodium hydroxide aqueous solution is added thereto to measure absorbance at 650 nm.

EXAMPLE 56

In a test tube, 40 μl of human serum (Fe 1200 μg/l, Cu 1090 μg/l) is placed and 3 ml of 0.1 M acetate buffer solution (pH 5.0) containing 4-amino-3-methyl-N-ethyl-N-(β-methanesulfonamidethyl)aniline in proportion of 4.2 mmole/l and sodium 1-naphthol-8-sulfonate in proportion of 1 mmole/l is added thereto. Using the same procedure as mentioned in Example 55, absorbance at 650 nm is measured.

EXAMPLE 57

In a test tube, 40 μl of human serum (Fe 1120 μg/l, Cu 1030 μg/l) is placed and 3 ml of 0.2 M acetate buffer solution (pH 5.0) containing 4-amino-3-methyl-N,N-diethylaniline in proportion of 8.4 mmole/l and saturated 1-(2′,4′,6′-trichlorophenyl)-3-(3′-aminobenzoylamino)-2-pyrazoline-5-one is added thereto. Using the same procedure as mentioned in Example 55, absorbance at 515 nm is measured.

EXAMPLE 58

A color developing solution A is prepared by dissolving 300 mg of 3-methyl-N-ethyl-N-(β-hydroxyethyl)aniline in 100 ml of isopropyl alcohol.

A color developing solution B is prepared by dissolving 300 mg of 4-aminoantipyrine in 100 ml of 5% acetic acid aqueous solution.

A color developing solution C is prepared by dissolving 10 mg of anhydrous ferric chloride in 100 ml of 5% acetic acid aqueous solution.

In a test tube, 200 μl of human serum is placed and 4.0 ml of the color developing solution A is added and mixed with stirring. The resulting mixture is centrifuged and 3.0 ml of supernatant liquid is separated from the precipitate. To the supernatant liquid, 0.5 ml of the color producing solution B is added and then 0.5 ml of the color developing solution C is added. The resulting mixture is allowed to stand at 37° C. in a constant temperature water bath for 60 minutes and absorbance at 560 nm ($E_1$) is measured. A reagent blank test is conducted similarly and absorbance at 560 nm ($E_{BL}$) is measured. Absorbance of the sample ($E_s$) is obtained from the following equation:

$$\text{Absorbance of sample} = E_s = E_1 - E_{BL}$$

The same procedures as mentioned above are repeated for a standard sample to measure absorbance of the standard sample ($E_{std}$). Peroxide value of the sample is obtained from the ratio of absorbance of the sample to absorbance of the standard sample.

EXAMPLE 59

A color developing solution A is prepared by dissolving 100 mg of 4-aminoantipyrine and 200 mg of 3-methyl-N-ethyl-N-(β-hydroxyethyl)aniline in 100 ml of a solution containing 2% by volume of acetic acid, 10% by volume of isopropyl alcohol and 88% by volume of water.

A color developing solution B is prepared by dissolving 20 mg of ferric chloride (hexahydrate) in 100 ml of 2% acetic acid aqueous solution.

In a test tube, 100 μl of human serum is placed and 1 ml of isopropyl alcohol is added thereto and mixed with stirring. The mixture is centrifuged and 200 μl of supernatant liquid is separated from the precipitate. To the supernatant liquid, 3.0 ml of the color developing solution A and 0.1 ml of the color developing solution B are added. The resulting mixture is allowed to stand at 37° C. in a constant temperature water bath for 60 minutes, and subsequently absorbance at 545 nm ($E_1$) is measured. A reagent blank test is conducted similarly and absorbance at 545 nm ($E_{BL}$) is measured. Peroxide value of the sample is obtained in the same manner as described in Example 58.

EXAMPLE 60

A color producing solution A is prepared by dissolving 150 mg of 3-methyl-N-ethyl-N-(β-hydroxyethyl)aniline and 30 mg of 4-aminoantipyrine in 100 ml of a mixture of carbon tetrachloride and ethanol (1:1 by volume).

A color producing solution B is prepared by dissolving 50 mg of anhydrous ferric chloride in 1 liter of ethanol.

In a test tube, 200 μl of human serum is placed and 1.0 ml of methanol is added thereto with stirring and subsequently 3.0 ml of hexane is added thereto and mixed with stirring. Then 2.0 ml of supernatant liquid is separated and 3.0 ml of the color developing solution A and then 0.5 ml of the color developing solution B are added. The resulting mixture is allowed to stand at 37° C. in a constant temperature water bath for 30 minutes, and then absorbance at 560 nm ($E_1$) is measured. A reagent blank test is conducted similarly and absorbance at 560 nm ($E_{BL}$) is measured. Peroxide value of the sample is obtained in the same manner as described in Example 58.

EXAMPLE 61

A color developing solution is prepared by dissolving 100 mg of 4-(p-dimethylaminoanilino)antipyrine and 50 mg of Mohr's salt ($(NH_4)_2Fe(SO_4)_2.6H_2O$) in 100 ml of 0.1 N sulfuric acid aqueous solution.

A standard solution of 100 nmoles/ml is prepared by dissolving 15.2 mg of cumene hydroperoxide in 1000 ml of isopropyl alcohol.

In three test tubes A, B and C, a human serum sample, a standard solution, and distilled water are placed independently in this order in an amount of 200 μl. To each test tube, 4.0 ml of isopropyl alcohol is added and stirred with a mixer two times for 5 seconds with an interval of 5 minutes. Subsequently, each test tube is centrifuged at 3000 r.p.m. for 5 minutes and 3.0 ml of each supernatant liquid is taken out and 1.0 ml of the color developing solution is added thereto. Each resulting mixture is heated at 37° C. for 10 minutes to develop color. Absorbance at 555 nm of each colored solution of test tubes A, B, and C is measured (each absorbance being $E_A$, $E_B$ and $E_C$) and the amount of peroxidic substance in the serum sample is calculated from the following equation:

$$\text{Content of peroxidic substances in the sample (nmole/ml)} = \frac{E_A - E_C}{E_B - E_C} \times 100$$

EXAMPLE 62

A color developing solution A is prepared by dissolving 300 mg of 3-methyl-N-ethyl-N-(β-hydroxyethyl)aniline in 100 ml of isopropyl alcohol.

A color developing solution B is prepared by dissolving 300 mg of 4-aminoantipyrine in 100 ml of 5% acetic acid aqueous solution.

A color developing solution C is prepared by dissolving a metallic compound as listed in Table 5 in 5% acetic acid aqueous solution.

In a test tube, 200 μl of human serum is placed and 4 ml of the color developing solution A is added thereto and mixed well with stirring. Subsequently, the sample is centrifuged and 3 ml of supernatant liquid is taken out and 0.5 ml of the color developing solution B is added thereto followed by the addition of the color developing solution C. The resulting mixture is allowed to stand at 37° C. in a constant temperature water bath for 60 minutes and absorbance at 560 nm is measured. Taking sensitivity of the case using Mohr's salt as the color developing solution as 1.00, sensitivity ratios of individual cases are listed in Table 5. For comparison, the result of the case wherein no color developing solution C is added is also listed in Table 5.

The same procedures as mentioned above are repeated for cumene hydroperoxide samples. The results are as shown in Table 5.

TABLE 5

| Run No. | Color developing Solution C | Concentration of metallic compound (w/v %) | Sensitivity ratio Serum | Sensitivity ratio Cumene hydroperoxide |
|---|---|---|---|---|
| 1 | $FeSO_4(NH_4)_2SO_4 \cdot 6H_2O$ | 0.003 | 1.00 | 1.00 |
| 2 | $Fe_2(SO_4)_3(NH_4)_2SO_4 \cdot 24H_2O$ | 0.003 | 0.73 | 0.78 |
| 3 | $NaVO_3$ | 0.003 | 0.63 | 0.60 |
| 4 | $(CH_3COO)_2Cu$ | 0.003 | 0.89 | 0.85 |
| 5 | None | 0 | 0.02 | 0.01 |

EXAMPLE 63

Tempura oil (0.5 ml) is added to 1 ml of carbon tetrachloride to give a sample solution.

A color developing solution A is prepared by dissolving 1.48 mmole of 4-aminoantipyrine and 8.4 mmole of N-ethyl-N-hydroxyethyl-3-methylaniline in 1 liter of a mixture of carbon tetrachloride and ethyl alcohol (1:1 by volume).

A color developing solution B is prepared by dissolving 200 mg of ferric chloride in 1 liter of ethyl alcohol.

To 0.5 ml of the sample solution, 3.0 ml of the color developing solution A and 0.1 ml of the color developing solution B are added and the resulting mixture is placed in a constant temperature water bath at 40° C. for 30 minutes to carry out the reaction. Then, absorbance at 567 nm is measured. The same procedure as mentioned above is repeated for carbon tetrachloride in place of the sample solution. Absorbance of the sample is obtained by subtracting the value of carbon tetrachloride from the value of the sample. The same procedures are repeated for a standard solution (an ethyl alcohol solution containing t-butyl hydroperoxide in amounts 3–80 μg/ml) to measure absorbance of the standard solution. From the calibration curve thus prepared, a peroxide value of the sample can be obtained.

In the next place, oxygen is introduced into ethyl oleate at 8° C. while irradiating with ultraviolet rays to produce ethyl oleate hydroperoxide. Peroxide values are obtained according to the method of this invention as to samples taken out with the lapse of time. For comparison, peroxide values of the samples are also determined by the iodine method. The results are as shown in Table 6.

TABLE 6

| Sample No. | 1 | 2 | 3 | 4 | 5 | 6 | 7 |
|---|---|---|---|---|---|---|---|
| The method of this invention | 5.5 | 24.6 | 28.8 | 40.1 | 55.4 | 69.5 | 81.9 |
| The iodine method | 5.7 | 27.0 | 34.4 | 44.8 | 57.8 | 74.0 | 86.8 |

As is clear from Table 6, the values obtained by the method of this invention are very close to those obtained by the iodine method which employs very strict conditions.

Degree of precision in measurement according to the method of this invention is compared with that of the iodine method and listed in Table 7.

TABLE 7

| | 1 | | 2 | |
|---|---|---|---|---|
| Sample No. | Method of this invention | Iodine method | Method of this invention | Iodine method |
| Procedure 1 | 24.6 | 27.0 | 40.1 | 44.8 |
| 2 | 24.8 | 26.5 | 41.0 | 45.0 |
| 3 | 25.0 | 27.3 | 40.3 | 44.5 |
| 4 | 24.0 | 27.0 | 39.5 | 44.7 |
| 5 | 24.0 | 27.3 | 39.7 | 45.1 |
| 6 | 24.5 | 26.7 | 39.7 | 45.0 |
| 7 | 25.2 | 26.5 | 40.0 | 44.8 |
| 8 | 25.2 | 27.3 | 39.8 | 44.7 |
| Mean value (x) | 24.7 | 27.0 | 40.0 | 44.8 |
| Standard Deviation | 0.48 | 0.35 | 0.47 | 0.19 |
| Coefficient of variation (%) | 1.9 | 1.3 | 1.2 | 0.4 |

As is clear from Table 7, degree of precision in measurement according to the method of this invention is very good and in the same degree as is obtained by the iodine method employing strict conditions (20° C., 10 minutes).

EXAMPLES 64–66

Preparation of reagents:

A color developing solution is prepared by dissolving 1.48 mmole of 4-aminoantipyrine and 8.4 mmole of N-ethyl-N-hydroxyethyl-3-methylaniline in 1 liter of a mixture of carbon tetrachloride and ethyl alcohol (1:1 by volume).

An iron(III) solution is prepared by dissolving 50 mg of ferric chloride (6 hydrate) in 1 liter of ethyl alcohol.

A standard solution: tert-Butyl hydroperoxide (200 mg) is dissolved in 100 ml of ethyl alcohol to give a standard solution for preservation, which is stored in a refrigerator in the dark. To 2.0 ml of the standard solution for preservation, ethyl alcohol is added to give 200 ml of a standard solution. The standard solution includes 20 μg of tert-butyl hydroperoxide per ml of the solution and has a peroxide value of 0.444 meq/kg.

Measuring procedures:

In Example 64, 0.5 ml of salad oil commercially available and 3.0 ml of the color developing solution are mixed in a test tube, and 0.5 ml of the iron(III) solution is added thereto. The resulting mixture is warmed at 40° C. in a constant temperature water bath for 30 minutes. Absorbance at 567 nm is measured and compared with the value of a blank test obtained in the same manner. A peroxide value of the sample is calculated from the calibration curve obtained in the same manner.

In Example 65, tempura oil used one time for cooking tempura is filtered and 1.0 ml of the filtered oil is diluted with ethyl alcohol to give 20 ml of a diluted solution. Using 0.5 ml of the diluted solution, the procedure of Example 64 is repeated and a peroxide value of the sample is calculated in the same manner as described in Example 64 taking the dilution percentage into consideration.

In Example 66, 0.5 ml of ethyl ether as a sample and 3.0 ml of the color developing solution are mixed in a test tube and 0.5 ml of the iron(III) solution is added thereto. The test tube is corked tightly and warmed in a constant temperature water bath at 40° C. for 30 minutes. Subsequently the same procedure as described in Example 64 is repeated and a peroxide value of the sample is calculated.

What is claimed is:

1. A method for determining lipoperoxides in a fluid sample obtained from a human being or other animal comprising:

(a) extracting a lipoperoxide from a sample of serum, blood plasma or blood with a solvent selected from the group consisting of a hydrocarbon, an alcohol, a halogenated hydrocarbo dimethylformamide, dimethylsulfoxide and N-methyl-pyrrolidone;

(b) contacting the extracted lipoperoxides with an oxidizable color reagent in the presence of a metallic compound produced from a metal which is able to have two or more valences to produce color; and (c) measuring the degree of coloring.

2. A method according to claim 1, wherein the oxidizable color reagent is a phenylenediamine derivative or aniline derivative.

3. A method according to claim 1, wherein the oxidizable color reagent is a mixture of 4-aminoantipyrine or 3-alkyl-2-benzothiazolinonehydrazone with an aniline derivative.

4. A method according to claim 1, wherein the oxidizable color reagent is a reaction product of 4-aminoantipyrine and an aniline derivative having the formula:

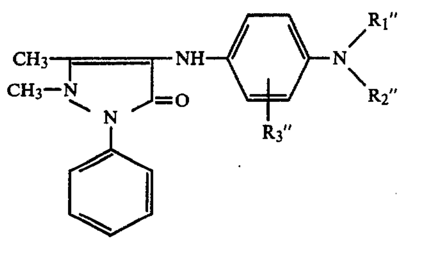

wherein R″1, and R″2 are independently hydrogen, alkyl having 1 to 3 carbon atoms, hydroxyalkyl having 1 to 3 carbon atoms, or phenyl; and R″3 is hydrogen, alkyl having 1 to 3 carbon atoms, sulfo, or a group of the formula X—$OSO_2$— in which X is an alkali metal, alkaline earth metal or ammonium.

5. A method according to claim 1, wherein the solvent is methanol, ethanol or propanol.

6. A method according to claim 1, wherein the metal producing the metallic compound is a transition metal.

7. A method according to claim 6, wherein the transition metal is iron, copper or vanadium.

8. A method according to claim 6, wherein the transition metal is iron, copper, manganese, cerium, cobalt, molybdenum, tungsten, or vanadium.

* * * * *